(12) United States Patent
Miyagawa

(10) Patent No.: US 6,500,929 B1
(45) Date of Patent: Dec. 31, 2002

(54) MEMBRANE-BOUND C1 INHIBITOR

(75) Inventor: Shuji Miyagawa, Ashiya (JP)

(73) Assignee: President of Osaka University, Suita (JP)

( * ) Notice: Subject to any disclaimer, the term of this patent is extended or adjusted under 35 U.S.C. 154(b) by 0 days.

(21) Appl. No.: 09/519,878

(22) Filed: Mar. 6, 2000

(30) Foreign Application Priority Data

Jul. 21, 1999  (JP) ............................................ 11-206535

(51) Int. Cl.⁷ ........................ A61K 35/16; A61K 35/14; A61K 39/00; C07K 1/00; C07K 14/00

(52) U.S. Cl. .................. 530/380; 530/350; 530/388.25; 530/395; 435/69.7; 424/145.1; 424/192.1; 930/10; 930/250

(58) Field of Search ............................ 530/350, 388.25, 530/380, 395; 435/69.7; 424/145.1, 192.1; 930/10, 250

(56) References Cited

U.S. PATENT DOCUMENTS 5,622,930 A    4/1997  Eldering et al.

FOREIGN PATENT DOCUMENTS

JP    9-510088    10/1997
JP    10-313865   12/1998

OTHER PUBLICATIONS

Wells et al. Additivity of Mutational Effects in Proteins, (1990) Biochemistry, vol. 29, No. 37, pp. 8509–8517.*

Ngo et al. Computational Complexity, Protein Structure Prediction and Levinthal Paradox, (1994) The Protein Folding Problem and Tertiary Structure Prediction, K. Merz, Jr. and S Le Grand, ed., Birkhauser, Boston, MA, Ch. 14, pp. 492–495.*

Matsunami et al. Database CAPlus on STN, Chemical Abstracts Service (Columbus, OH, USA), Acc. No. 2000: 48491, Organ Biol. (1999) 6(4): 67–71, abstract.*

Randazzo et al. Synthesis of C1 Inhibitor (C1–INA) by a Human Monocyte–Like Cell Line, U937, (1985) J. Immunol. vol. 135, No. 2, pp. 1313–1319.*

Schmaier et al. Expression of Platelet C1 Inhibitor, (1993), vol. 82, No. 2, pp. 465–474.*

M. Lener, et al., Eur. J. Biochem., vol. 254, pp. 117–122, "Molecular Cloning, Gene Structure and Expression Profile of Mouse C1 Inhibitor", 1998.

* cited by examiner

*Primary Examiner*—Christopher S. F. Low
*Assistant Examiner*—Holly Schnizer
(74) *Attorney, Agent, or Firm*—Oblon, Spivak, McClelland, Maier & Neustadt, P.C.

(57) ABSTRACT

The present invention provides an mbCRP capable of effectively suppressing complement activity and completely inhibiting generation of intermediates damaging a transplanted tissue during the complement activation. To be more specific, the present invention provides a membrane-bound C1 inhibitor comprising a protein containing a functional domain of a water-soluble C1 inhibitor and an anchor molecule attached to an end and/or an interior of the protein.

16 Claims, 5 Drawing Sheets

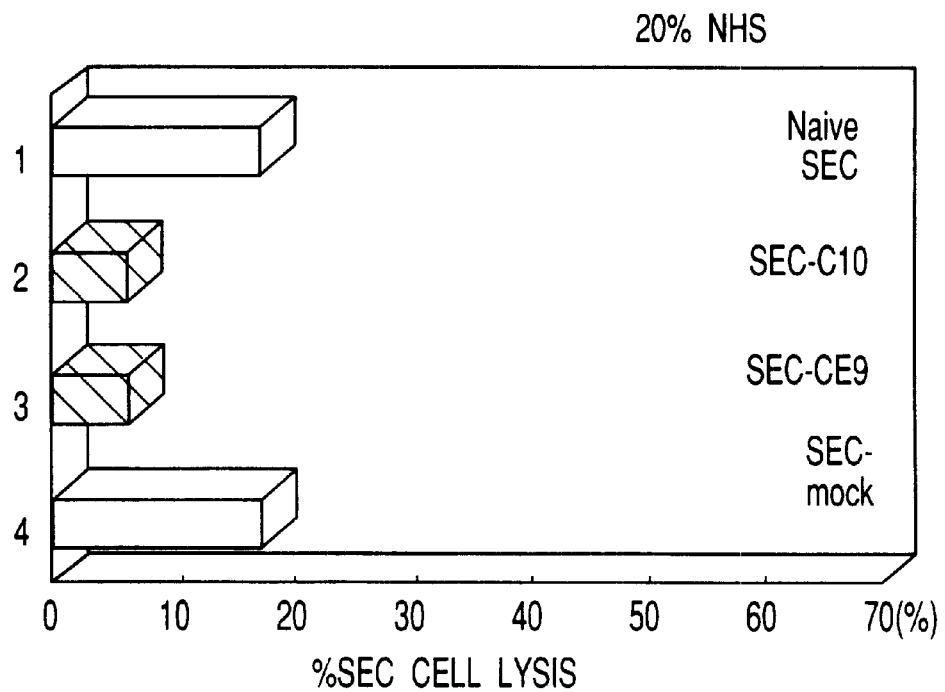
F I G. 7A
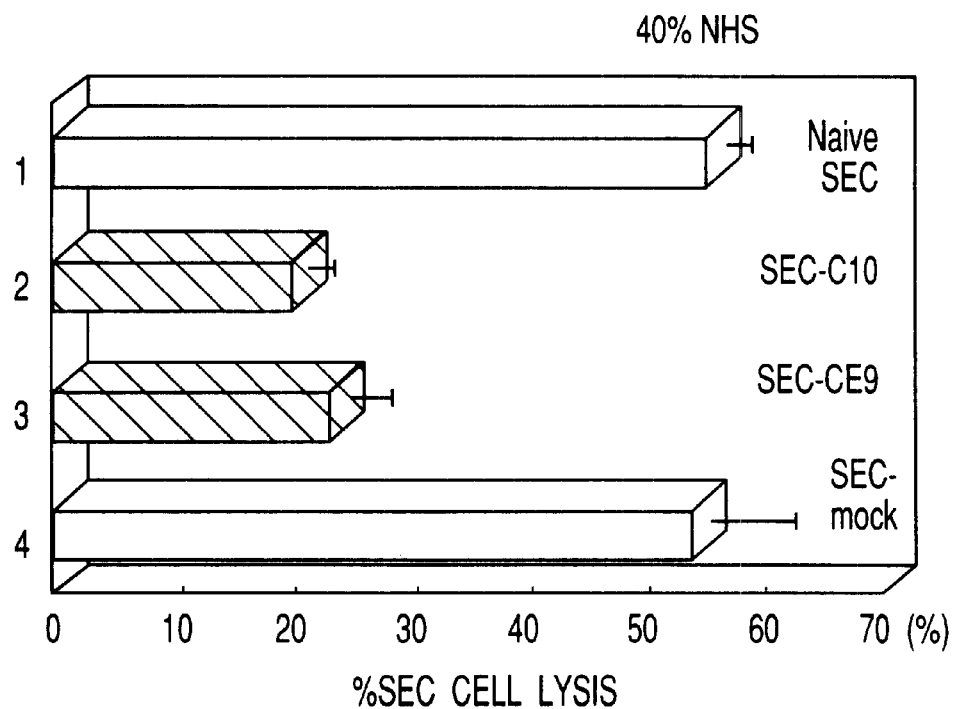
F I G. 7B

MEMBRANE-BOUND C1 INHIBITOR

CROSS-REFERENCE TO RELATED APPLICATION

This application is based upon and claims the benefit of priority from the prior Japanese Patent Application No. 11-206535, filed Jul. 21, 1999, the entire contents of which are incorporated herein by reference.

BACKGROUND OF THE INVENTION

The present invention relates to a membrane-bound complement regulatory protein capable of suppressing an initial reaction of a complement pathway which causes a hyperacute rejection in a subject (donated organ) when organs, tissues or cells are transplanted. The present invention also relates to a nucleic acid molecule encoding the membrane-bound complement regulatory protein and a vector having the nucleic acid molecule. The present invention further relates to a cell, a tissue and an organ having the vector introduced therein. Moreover, the present invention relates to a transgenic animal, particularly, a transgenic swine in which a gene of the membrane-bound complement regulatory protein is introduced.

Organ transplantation is an extremely useful radical treatment and completely differs from a conventional symptomatic treatment. Recently, transplantation of organs such as kidney, cornea, liver, and heart has been frequently and widely performed to recover dysfunction or hypofunction of the organs.

The most significant problem which should be overcome in the organ transplantation is a rejection. In the case of kidney transplantation from human to human, which is one of the most widely performed organ transplantation, a hyperacute rejection occurs within several minutes after transplantation in a case where blood types do not match with each other, with the result that severe propagated thrombosis occurs around the transplanted organ. It has been elucidated that the hyperacute rejection at the time of allotransplantation (the donor and recipient belong to the same species) is caused by activating a complement pathway by binding C1 (a first component of complement) to an immune complex, which consists of a blood type determinant glycogenic antigen of a graft and an antibody against the blood type determinant glycogenic antigen inherently present as a natural antibody in the recipient. In the case of xenotransplantation (the donor and recipient belongs to different species), the rejection would be more serious since all substances not present in the recipient may come to be possible xenotransplantation antigens. Therefore, the rejection is a big problem of preventing clinical application of the xenotransplantation which enables donation of numerous organs.

As described above, the primary issue to be solved in the organ transplantation is to inhibit the hyperacute rejection occurring immediately after transplantation. Since the hyperacute rejection is caused by activating the complement pathway as previously described, if a suppressive substance for the pathway is introduced into the organ to be transplanted in advance, the hyperacute rejection can be inhibited.

Currently, based on the aforementioned idea, several manufacturers actually put production of transgenic swine into practice by introducing genes of endogenous human membrane-bound complement regulatory proteins (hereinafter referred to as "mbCRPs"), such as CD 46 (membrane cofactor protein; MCP), CD55 (decay accelerating factor, DAF) and CD59 (HRF 20), and actually apply to the xenotransplantation. The term "complement regulatory protein (hereinafter referred to an "CRP")" used herein refers to a protein regulating the complement pathway in a living body. Almost all the CRPs including the aforementioned three proteins have a function of regulating a complement activity. Therefore, if an organ of the transgenic animal having the CRP introduced therein is transplanted to a recipient, the complement pathway of the recipient can be suppressed.

Now, referring to FIG. 1, working points of the mbCRPs, namely, CD46, CD55 and CD59 in the compliment pathway will be explained. At first, the working point of CD46 resides in the reaction represented by a reference numeral (3) in FIG. 1. CD 46 functions as a cofactor of factor I in converting C3b and C4b into inactivated forms. C3b is a molecule playing a pivotal role in the complement pathway. More specifically, C3b plays a role in ① activating a C3 convertase (YC3bBbP in FIG. 1) of an alternative pathway,
② converting C3 convertases (YC4b2a and YC3bBbP in FIG. 1) into a C5 convertase (YC4b2a3b),
③ mediating binding to a complement receptor type I, CR1, of a blood cell.

On the other hand, the working point of CDS5 resides in the reaction represented by a reference numeral (2) in FIG. 1. More specifically, CD 55 promotes dissociation of C2a* from the C3 convertase C4b2a in the classical complement pathway and simultaneously promotes dissociation of Bb from the C3 convertase YC3bBbP in the alternative complement pathway. The working point of CD59 resides in the reaction represented by a reference numeral (4) in FIG. 1. Different from CD46 and CD55, CD59 does not act on the C3 convertase but inhibits the conversion of C9 to ZC5b-9, which is a final step of the complement pathway.

These three mbCRPs can regulate respective steps of the complement pathway in the working mechanisms mentioned above. In addition, since these three proteins can be maintained with a high density at a rejection site due to the binding onto the membrane, they play an effective role to some extent in suppressing the complement pathway.

However, these mbCRPs have the following problems.

First, it is difficult to express CD46 in a transgenic animal abundantly. In addition, CD46 has a drawback in that it is poor in complement suppressing ability when bounded onto the membrane, compared to the other two factors.

It is known that CD59 regulates complement at the end of a cascade, so that C4, C3, and C5 present in the middle of the cascade are activated to generate anaphylatoxins, C4a, C3a and C5a, respectively, which damage a graft.

On the other hand, even if CD55, which is the most promising regulatory factor, is employed, the reactions up to C4 take place, with the result that C4a is generated and C4b is deposited on a graft.

BRIEF SUMMARY OF THE INVENTION

The present invention has been made to overcome the aforementioned problems. An object of the present invention is to provide an mbCRP capable of effectively repressing a complement pathway and completely inhibiting generation of intermediates damaging a transplanted tissue in the complement pathway.

To be more specific, the present invention provides a membrane-bound C1 inhibitor comprising a protein containing a functional domain of a water-soluble C1 inhibitor and an anchor molecule attached to an end and/or an interior portion of the protein.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 7A and 7B show graphs showing the effect of the membrane-bound C1 inhibitors on suppressing the complement-mediated lysis of the Chinese hamster ovary cells.

DETAILED DESCRIPTION OF THE INVENTION

The present invention provides a membrane-bound C1 inhibitor artificially produced by adding an anchor molecule to naive water-soluble C1 inhibitor.

The "C1 inhibitor" (simply referred to as "C1-INH") used herein refers to a protein inhibiting a serine protease activity of C1 which is activated by binding with an immunoglobulin present in an immune complex. The "water soluble C1-INH" refers to an endogenous C1-INH present in serum and thus equivalent to "serum C1-INH".

The working point of the C1-INH in the complement pathway resides in the initial reaction of the pathway. Therefore, if the C1-INH is used, it is possible to effectively suppress the activation of the pathway without harmful intermediates which may be generated in the middle of the pathway.

The specificity of the C1-INH to species is not strict unlike CD46 and CD55. Therefore, it is not necessary that the water soluble C1-INH to be used in producing the membrane-bound C1-INH of the present invention be derived from the species to which a recipient belongs; however, preferably the same as or related thereto. More specifically, in the case where the recipient is a human being, a murine water-soluble C1-INH may be used, however, it is preferable to use a human water-soluble C1-INH. The amino acid sequence. (SEQ ID No:2) and nucleotide sequence (SEQ ID No: 1) of the human water-soluble C1-INH, as well as the amino acid sequence (SEQ ID No: 4) and nucleotide sequence (SEQ ID No:3) of the murine C1-INH are listed in the sequence list attached hereto.

The "protein" used herein refers to the polyamino acid having at least two amino acids connected by a peptide bond, including not only a simple protein but also a conjugated protein containing constituents other than amino acids, such as sugars, lipids and nucleic acids.

Figure 1:
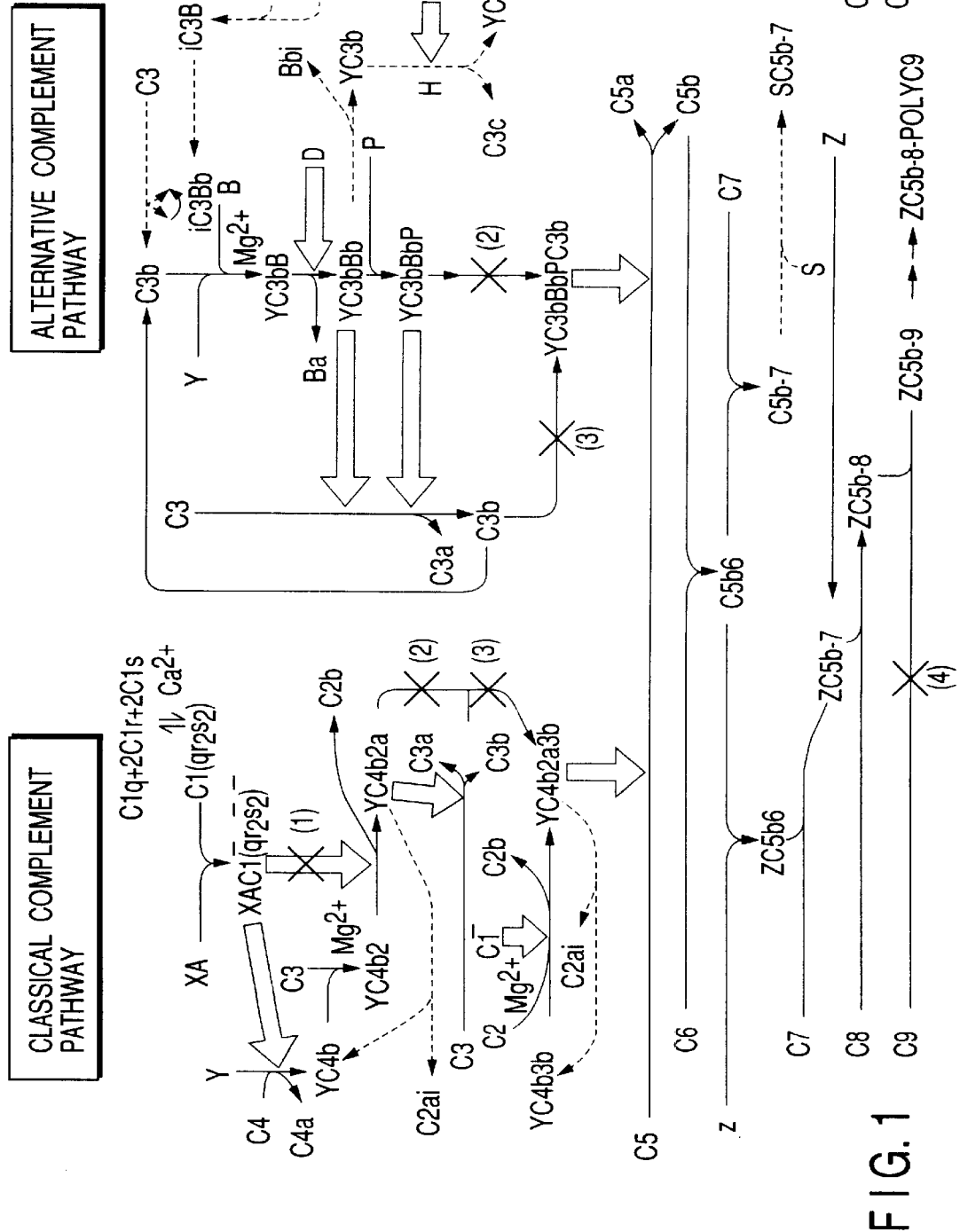
FIG. 1 is a view for explaining working points of CRPs in a complement pathway.
Figure 2:
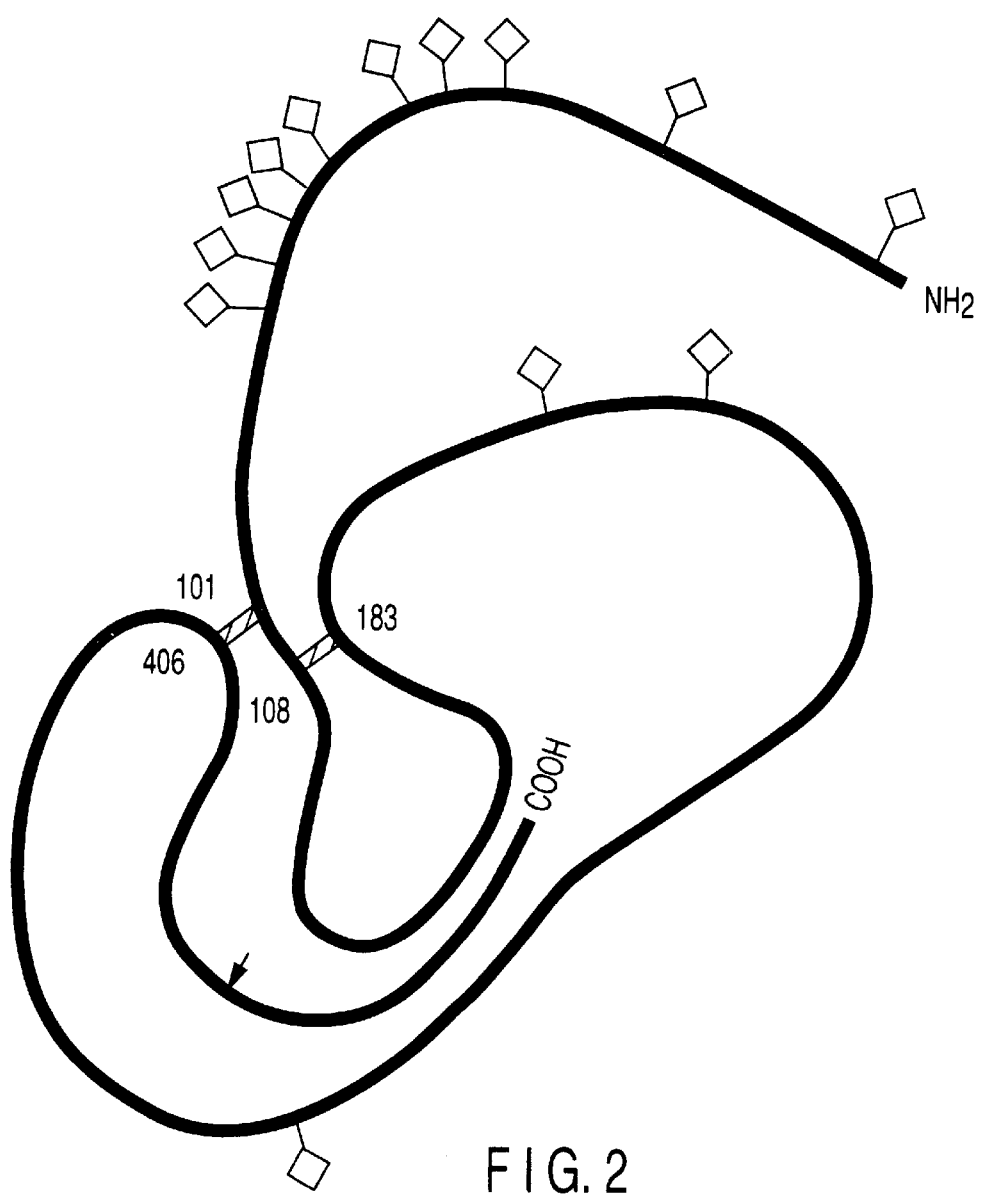
FIG. 2 is a schematic illustration showing a configuration and an active center of C1-INH.

The "functional domain" refers to a region of a protein having a direct and indispensable role in the function of a predetermined protein. Therefore, if a protein containing a functional domain of C1-INH is produced and allowed to be expressed in an organ or a tissue of a donor, the complement pathway is successful suppressed. The active center of the human C1-INH resides in an amino acid sequence present in the C terminal portion (i.e., arginine at position 444 shown in SEQ ID NO: 1 (which corresponds to position 466 in SEQ ID NO: 2) and threonine at position 445 shown in SEQ ID NO: 1 (which corresponds to position 467 SEQ ID NO: 2), (since a signal peptide consisting of 22 amino acids is excised out from the C1-INH shown in FIG. 2, position 1 in FIG. 2 and shown as position 1 in the encoded amino acid sequence shown in SEQ NO: 1 corresponds to position 23 of the C1-INH of the SEQ ID NO:2)). The active center is known to be cleaved by binding to a subunit of C1, namely, C1s or the like. When the active center is cleaved, arginine at position 444 shown in SEQ ID NO: 1 (which corresponds to position 466 in SEQ ID NO: 2) is bonded to activated serine on a β chain at the C terminal side of the C1s or the like. Furthermore, not only cysteine molecules at position 101 and 406 shown in SEQ ID NO: 1 (which correspond to positions 123 and 428, respectively, in SEQ ID NO: 2) but also cysteine molecules at position 108 and 183 shown in SEQ ID NO: 1 (which correspond to positions 130 and 205 in SEQ ID NO: 2) form disulfide bonds, respectively, contributing to retention of the configuration of the C1-INH. From the aforementioned structure, it is considered that the amino acid sequence at least from positions 101 to 445 shown in SEQ ID NO: 1 (which corresponds to positions 123 to 467 in SEQ ID NO: 2) is indispensable to the function of the human C1-INH. It is thus presumed that this portion is a functional domain. The similar structure to the functional domain is conserved in the murine C1-INH. The amino acid sequence of the active center of the murine C1-INH resides in arginine at position 448 and serine at position 449 (shown in SEQ ID NO: 4 at positions 470 and 471, respectively). The cysteine molecules at positions 101 and 406 of the human C1-INH correspond to those of positions 106 and 410 of the murine C1-INH, respectively (positions 106 and 410 of the murine sequence are shown as positions 128 and 432 of SEQ ID NO: 4, respectively). The cysteine molecules at positions 108 and 183 correspond to those of positions 113 and 188, respectively (positions 113 and 188 of the murine sequence are shown as positions 135 and 210 of SEQ ID NO: 4, respectively). Therefore, by analogy with the human C1-INH it is possible to presume functional domains of C1-INHs of mammalian animals other than human beings.

A single amino acid or several amino acids may be deleted from, replaced for, or added to the functional domain of the water soluble C1-INH, as long as the functional domain retains a function in regulating the complement pathway. Note that "retaining a function in regulating the complement pathway" means "having a function in suppressing the complement activation substantially applicable in organ transplantation".

In the modification of the molecule, it is required that

① cysteine molecules involved in the disulfide bond are not modified; and

② the amino acids of the active center include basic amino acids, non-charged polar amino acids, and nonpolar amino acids.

Examples of the basic amino acids include lysine, arginine and histidine. Examples of the non-charged polar amino acids include serine, threonine, tyrosine, asparagine and glutamine. Preferable examples of the non-charged polar amino acids are threonine and serine constituting an active center of naive human and murine C1-INHs, and tyrosine having a hydroxyl group forming the active center.

Examples of the nonpolar amino acids include alanine, glycine, valine, isoleucine, proline, phenylalanine, methionine, tryptophan, and cysteine. Preferable examples of the nonpolar amino acids are alanine and glycine having the same sizes as threonine and serine.

The "anchor molecule" refers to a molecule for use in incorporating a protein into a membrane, in other words, a molecule for constructing a membrane-bound protein. More specifically, the anchor molecules may include, but not limited to, ① transmembrane portions mainly consisting of a sequence of hydrophobic amino acid residues;

② aliphatic acids such as myristic acid and palmitic acid;

③ phospholipids such as glycosylphosphatidylinositol (hereinafter referred to as "GPI");

④ terpenes such as a prenyl group and a farnesyl group;

⑤ known molecules present in naive membrane-bound proteins such as linear hydrocarbons and branched hydrocarbons; or ⑥ a combination of ① to ⑤.

When the transmembrane portion of the transmembrane protein is used as the anchor molecule, a transmembrane portion other than the CRP, that is, a transmembrane portion contained in I-IV type transmembrane proteins may be used. The transmembrane portion of the transmembrane protein is a particularly preferable anchor molecule, since it can be transduced into another species by connecting to cDNA of the C1-INH.

The membrane-bound C1-INH of the present invention is prepared by adding the anchor molecule to the water-soluble C1-INH or the functional domain thereof. The anchor molecule may be synthetically added to the water-soluble C1-INH. However, it is extremely preferable, in consideration of handling and an expression efficiency on the membrane, that the anchor molecule be added by preparing a construct having a gene encoding the water soluble C1-INH and the nucleotide sequence encoding the anchor molecules, and expressing the construct in a living body. In the case where a non-proteinaceous anchor molecule is added, a nucleotide encoding the amino acid sequence which serves as a signal for adding the anchor molecule in an endoplasmic reticulum or a cytoplasm, may be connected to the water soluble C1-INH gene. The amino acid sequence serving as a signal for adding an aliphatic acid, a terpene, GPI or the like is known well. For example, the amino acid sequence serving as a signal for adding GPI is known. The amino acid sequence is cleaved and removed in the endoplasmic reticulum. The nucleic acid sequence (SEQ ID No:5) of GPI addition signal of CD55 and the amino acid sequence thereof (SEQ ID No:6) are listed in the sequence list attached hereto. Note that it is not necessary for the anchor molecule to be derived from the same species as a donor.

To allow the membrane-bound C1-INH to express efficiently on a cell membrane, a signal peptide must be bonded to the N terminal of the water-soluble C1-INH.

If the nucleotide encoding the GPI is linked to the water-soluble C1-INH gene and introduced into an organ or a tissue to be transplanted, it is possible to express the membrane-bound C1-INH having GPI as the anchor molecule on a cell membrane of the organ or tissue to be transplanted.

To inhibit a complement activation taking place on the cell membrane, the membrane-bound C1-INH of the present invention should be prepared in such a manner that at least its functional domain is exposed outside the cell and GPI is preferably added to the C terminal end of the water-soluble C1-INH or the proximity thereto.

As mentioned above, according to present invention, it is possible to obtain the membrane-bound C1-INH having an inhibitory activity for the complement pathway equivalent to that of water soluble C1-INH. The membrane-bound C1-INH having "equivalent" activity means that its activity is at least 50% of that of water soluble C1-INH. That is, the membrane-bound C1-INH has an inhibitory activity for complement pathway substantially applicable to organ transplantation.

Another object of the present invention is to provide a nucleic acid molecule encoding the membrane-bound C1-INH. The "nucleic acid molecule" used herein includes both a DNA molecule and an RNA molecule. In the case where the anchor molecule is protein as described above, the nucleic acid molecule encoding the membrane-bound C1-INH comprises the water soluble C1-INH gene and nucleotides encoding the anchor molecule. In the case where the anchor molecule is not a protein, the nucleic acid molecule comprises a water-soluble C1-INH gene and nucleotides encoding an amino acid sequence serving as a signal for adding the anchor molecule in a donor cell.

A further object of the present invention is to provide a vector for use in expressing a nucleic acid molecule encoding the membrane-bound C1-INH in the organ or tissue to be transplanted. If the nucleic acid molecule encoding the membrane-bound C1-INH is inserted into the vector and then introduced into the organ or tissue to be transplanted by using a known method such as microinjection, electroporation or lipofection, it is possible to transfer the nucleic acid molecule encoding the membrane-bound C1-INH into a donor.

The "vector" used herein includes both a virus vector and a non-virus vector. The virus vector may be a vector consisting of a gene of an infectious virus such as retrovirus and adenovirus and a sequence for expressing the nucleic acid molecule encoding C1-INH in the organ or tissue to be transplanted (promoter sequence, poly A region and the like). A preferable virus vector is a retrovirus vector. The gene transfer using the retrovirus vector is known to those skilled in the art. The non-virus vector may be a vector having a sequence required for self-replication in bacteria such as *Escherichia coli* and a sequence for expressing the nucleic acid molecule encoding C1-INH in the organ or tissue to be transplanted (promoter sequence, poly A portion), which is added to the sequence.

The method of introducing the nucleic acid molecule into a cell is not limited to the method using a vector. Depending upon a type of the organ to be transplanted, a sequence consisting of the nucleic acid molecule encoding the membrane-bound C1-INH and a sequence for expressing the nucleic acid molecule, may be introduced by microinjection.

The present invention also includes the transgenic animals, organs, tissues and cells into which the membrane-bound C1-INH is introduced. The membrane-bound C1-INH may be introduced into any mammalian animal, however, swine and simian are particularly preferable. The organs into which the membrane-bound C1-INH is to be introduced include, but not limited to, lung, kidney, heart, liver, pancreas, and a digestive tract such as small intestine. The tissues into which the membrane-bound C1-INH is to be introduced include, but not limited to, cornea, meniscus, brain tissues, skin, subcutaneous tissue, endothelial tissue, bone, muscle and the like. The cells into which the membrane-bound C1-INH to be introduced include, but not limited to, all cells constituting the aforementioned organs and tissues, in particular, a pancreatic cell and a brain cell, as well as a fertilized egg cell and an embryonic stem cell. Now, the present invention will be explained more specifically with reference to Examples, which should not be construed as limiting the scope of the present invention.

EXAMPLE 1

Figure 3:
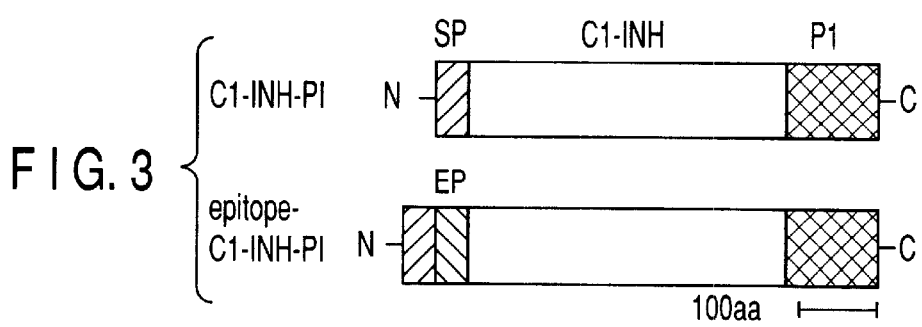
FIG. 3 includes schematic illustrations showing structures of the membrane-bound C1 inhibitors used in Example 1.

In this example, how to express the membrane-bound C1-INH shown in FIG. 3 on an animal cell membrane will be explained.

The membrane-bound C1-INH was constructed by connecting a GPI portion of CD55 to C terminal of the water-soluble C1-INH (hereinafter referred to as C1-INH-GPI). In this example, an epitope tag (FLAG tag) for use in detection was added to the C terminal of the signal peptide of C1-INH-GPI to thereby prepare the membrane-bound C1-INH (hereinafter referred to as FLAG-C1-INH-GPI) (see FIG. 3, lower graph).

In this example, to express C1-INH-GPI and FLAG-C1-INH-GPI on an animal cell membrane, cDNAs of them were prepared and transfected into Chinese hamster ovary cells by electroporation and transfected into swine vascular endothelial cells by lipofection.

Expression of C1-INH-GPI on both the Chinese hamster ovary cell and swine vascular endothelial cell were checked by a flow cytometer using a fluorescent labeled polyclonal antibody against C1-INH-GPI. The results are shown in FIGS. 4A–4E. C1-INH-GPI was stably expressed on the cell membrane of a plurality of the CHO strains (in FIGS. 4A and 4B, hatched portion).

Figure 4A:
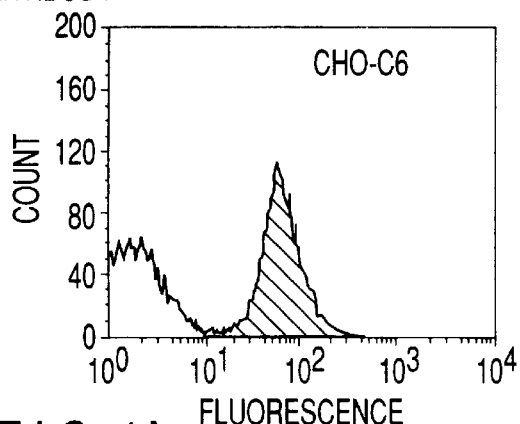
FIGS. 4A to 4E include graphs demonstrating that a membrane-bound C1 inhibitor is expressed in a Chinese hamster ovary cell and a porcine vascular endothelial cell.
Figure 4B:
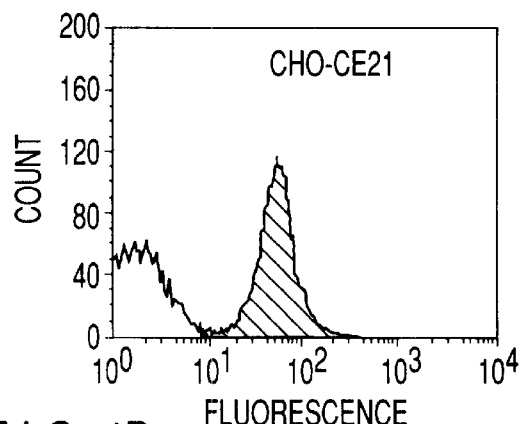
Figure 4C:
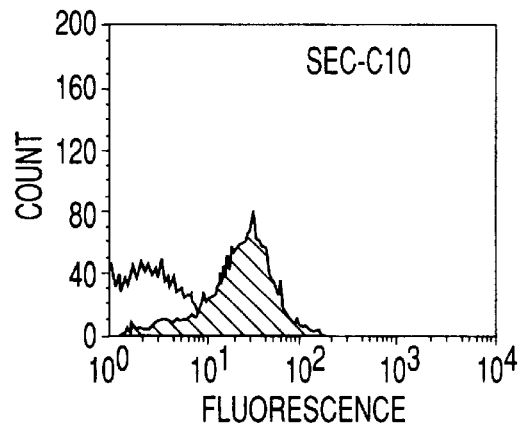
Figure 4D:
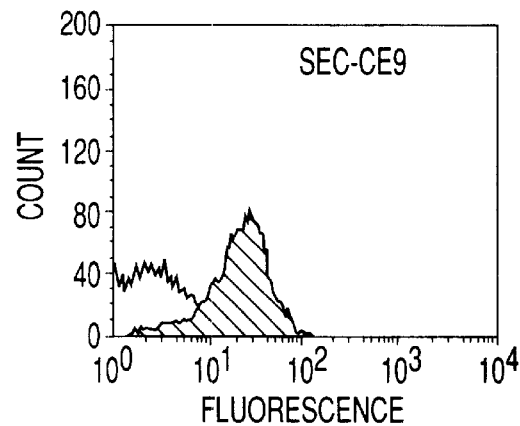

Similarly, C1-INH-GPI was stably expressed also on the cell membrane of a plurality of the SEC strains (FIGS. 4C and 4D, hatched portion).

The results mentioned above demonstrate that the C1-INH having GPI added thereto as the anchor molecule, can be expressed stably on the cell membranes of various animals.

Figure 4E:
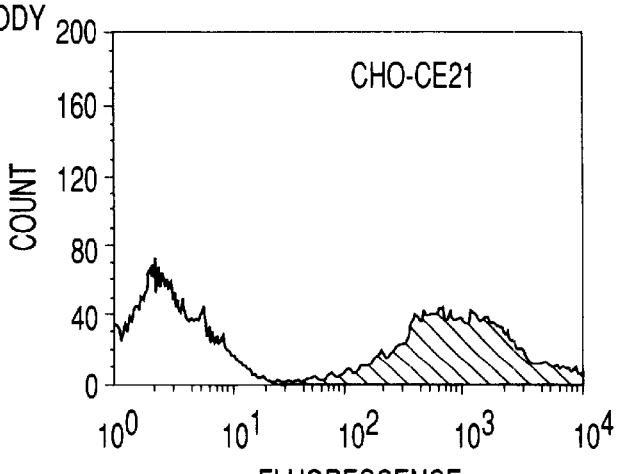

Expression of FLAG-C1-INH-GPI on the CHO cells was checked by a flow cytometer using a fluorescent labeled anti-FLAG monoclonal antibody. The results are shown in FIG. 4E. Fluorescent marker was also detected using the anti-FLAG monoclonal antibody. It was therefore demonstrated that the FLAG-C1-INH-GPI is expressed on the cell membrane of the CHO cell. Furthermore, Scatchard plot analysis was carried out using the anti-FLAG monoclonal antibody (M2). As a result, it was confirmed that the FLAG-C1-INH-GPI molecule was expressed in an amount of $51.3\pm3.7\times10^4$/cell in the case of CHO-CE21, and in an amount of $13.3\pm2.3\times10^4$/cell in SEC-CE9.

Figure 5:
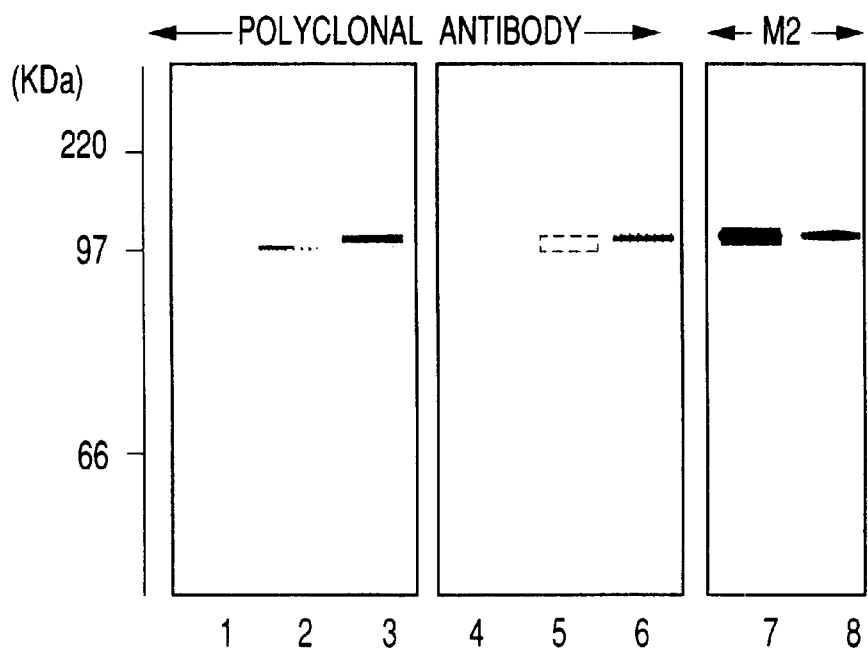
FIG. 5 shows the results of Western blotting of a protein extracted from the Chinese hamster ovary cells and the porcine vascular endothelial cells having a cDNA of a membrane-bound C1 inhibitor introduced therein, blotted with an anti membrane-bound C1 inhibitor antibody.

Proteins were extracted from those cells and Western blot was performed by using the polyclonal antibody and the monoclonal antibody. The results are shown in FIG. 5.

Lanes 1–3 and 7 are the results of the Western blot of the CHO cells. Lanes 4–6 and 8 are the results of the Western blot of the SEC cells. Lanes 1–6 are the results of the Western blot using the polyclonal antibody. Lanes 7 and 8 are the results of the Western blot using the monoclonal antibody.

Bands were detected at expected positions excluding the cells (lanes 1–4) into which no gene was transfected.

This example demonstrates that the membrane-bound C1 inhibitor can be artificially prepared by adding the anchor molecule to the water-soluble inhibitor and allowed to express on the cell membrane of various cells.

EXAMPLE 2

In this example, the inhibitory effect of the C1-INH-GPI on the complement-mediated cytotaxicity was checked.

First, an antibody against CHO cells was reacted with the CHO cells having expressed C1-INH-GPI (CHO-C6 and CHO-CE21). Thereafter, 40% human serum (NHS) containing a complement component was added thereto. Then, the inhibitory effect of C1-INH-GPI against the human complement was checked. The results are shown in FIGS. 6, 7A and 7B.

Figure 6:
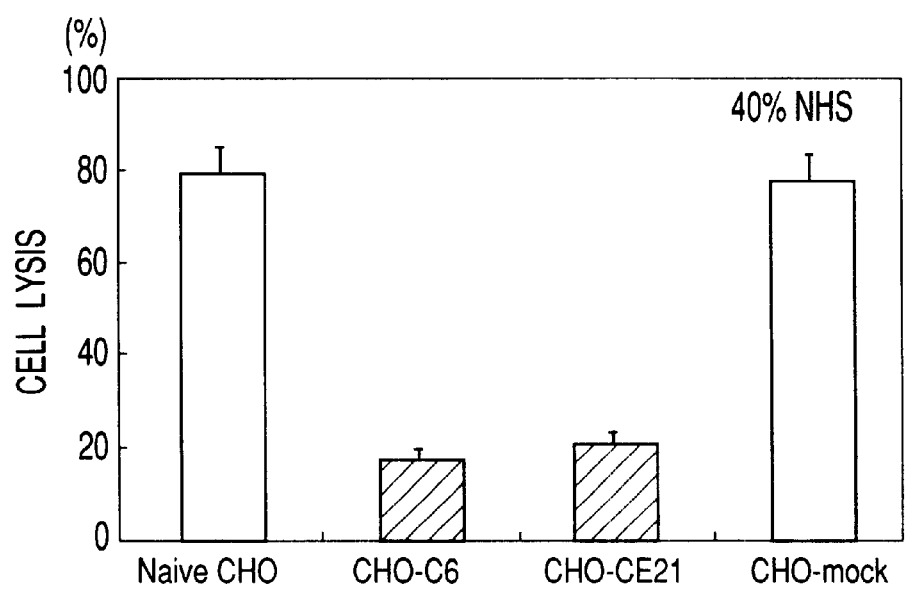
FIG. 6 is a graph showing the effect of the membrane-bound C1 inhibitor on suppressing the complement-mediated lysis of the Chinese hamster ovary cells.

As is apparent from FIG. 6, in naive CHO having no C1-INH-GPI introduced therein and in CHO-mock (open columns on both sides) to which only transfection is applied without C1-INH-GPI, about 80% of cells are lysed by the human complement. Whereas, in the cells in which C1-INH-GPI was expressed (hatched columns), only about 20% of the cells were lysed. This experiment demonstrated that C1-INH-GPI can suppressed the human complement-mediated CHO cell lysis, by about 75%.

Then, the inhibitor effect of C1-INH-GPI against the complement-mediated SEC cell lysis, was checked.

The 20% and 40% human serums containing the natural antibody and the complement were reacted with the SEC cell (SEC-CdO and SEC-CE9) having C1-INH-GPI expressed therein. Then, the effect of the human complement upon suppressing damage of the cell was observed.

As shown in FIG. 7A, 20% or less naive SEC and SEC-mock (columns 1 and 4) are lysed by the 20% human serum. Compared to this, the SEC in which C1-INH-GPI was expressed were lysed by only several % (columns 2 and 3). As described, in the SEC cells having C1-INH-GPI expressed on the membrane, the lysis due to the complement is reduced to 65–72%.

When the 40% human serum was added (FIG. 7B), in the naive SEC and SEC-mock (columns 1 and 4), about 55% of the cells was lysed. However, in the SEC cells having C1-INH-GPI expressed therein, SEC cells were lysed by about 20% (Columns 2 and 3). As described, when C1-INH-GPI is expressed on the membrane of the SEC cell, the complement-mediated lysis is reduced by 59–65%.

As shown above, this example demonstrated that the complement-mediated lysis is suppressed by 60–75% in the cells having C1-INH-GPI expressed on the cell membrane.

The membrane-bound C1 inhibitor of the present invention, due to its membrane-bound property, can remain enriched on the cell membrane compared to the water soluble C1 inhibitor. The complement reaction inducing hyperacute rejection occurs on a cell membrane in the organ transplantation. This feature of the present invention is therefore extremely effective in inhibiting the hyperacute rejection at the time of organ transplantation. More specifically, to obtain the same effect as in the membrane-bound C1 inhibitor of the present invention by using the water-soluble C1 inhibitor, the water-soluble C1 inhibitor is presumably required in an amount of 50–1000 times of that of the membrane-bound C1 inhibitor.

The membrane-bound C1 inhibitor of the present invention inhibits an initial reaction of the complement activation. Therefore, the complement activation can be suppressed extremely effectively, without the generation of noxious intermediates in the complement pathway.

If the organs, tissues and cells having the membrane-bound C1 inhibitor according to the present invention having such an effect expressed therein, are used, the hyperacute rejection is suppressed at the time the organ is transplanted. Therefore, the organs, tissues and cells in which the membrane-bound C1 inhibitor of the present invention is expressed are suitable for transplantation, particularly xenotransplantation.

Furthermore, the transgenic animals into which the membrane-bound C1 inhibitor gene is introduced, are useful to obtain such organs, tissues and cells.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A membrane-bound type C1 inhibitor, comprising:
   a protein having a functional domain of a water soluble C1 inhibitor, said protein comprising at least an amino acid sequence from positions 123 to 467 of SEQ ID NO. 2; and
   an anchor molecule added to a C-terminal of the functional domain of a C1 inhibitor protein, wherein the anchor molecule is capable of incorporating the water soluble C1 inhibitor protein into a cell membrane.

2. A membrane-bound type C1 inhibitor according to claim 1, wherein said anchor molecule is either glycosyl phosphatidylinositol or a transmembrane portion of a transmembrane protein.

3. A membrane-bound type C1 inhibitor according to claim 1, wherein said anchor molecule is glycosyl phosphatidylinositol.

4. A membrane-bound type C1 inhibitor according to claim 1, wherein said anchor molecule is a transmembrane portion of a transmembrane protein.

5. A membrane-bound type C1 inhibitor, comprising:
   a protein having a functional domain of a water soluble C1 inhibitor, said protein comprising at least an amino acid sequence from positions 128 to 471 of SEQ ID No. 4; and an anchor molecule added to a C-terminal of the functional domain of a C1 inhibitor protein, wherein the anchor molecule is capable of incorporating the water soluble C1 inhibitor protein in to a cell membrane.

6. A membrane-bound type C1 inhibitor according to claim 5, wherein said anchor molecule is either glycosyl phosphatidylinositol or a transmembrane portion of a transmembrane protein.

7. A membrane-bound type C1 inhibitor according to claim 5, wherein said anchor molecule is glycosyl phosphatidylinositol.

8. A membrane-bound type C1 inhibitor according to claim 5, wherein said anchor molecule is a transmembrane portion of a transmembrane protein.

9. A membrane-bound type C1 inhibitor, comprising:

a water-soluble C1 inhibitor protein having the amino acid sequence from positions 23 to 500 of SEQ ID NO: 2; and an anchor molecule added to the C-terminal of the functional domain of the C1 inhibitor protein, wherein the anchor molecule is capable of incorporating the water soluble C1 inhibitor protein into a cell membrane.

10. A membrane-bound type C1 inhibitor according to claim 9, wherein said anchor molecule is either glycosyl phosphatidylinositol or a transmembrane portion of a transmembrane protein.

11. A membrane-bound type C1 inhibitor according to claim 9, wherein said anchor molecule is glycosyl phosphatidylinositol.

12. A membrane-bound type C1 inhibitor according to claim 9, wherein said anchor molecule is a transmembrane portion of a transmembrane protein.

13. A membrane-bound type C1 inhibitor, comprising:

a water-soluble C1 inhibitor protein having the amino acid sequence from positions 23 to 504 of SEQ ID NO: 4; and an anchor molecule added to the C-terminal of the functional domain of the C1 inhibitor protein, wherein the anchor molecule is capable of incorporating the water soluble C1 inhibitor protein into a cell membrane.

14. A membrane-bound type C1 inhibitor according to claim 13, wherein said anchor molecule is either glycosyl phosphatidylinositol or a transmembrane portion of a transmembrane protein.

15. A membrane-bound type C1 inhibitor according to claim 13, wherein said anchor molecule is glycosyl phosphatidylinositol.

16. A membrane-bound type C1 inhibitor according to claim 13, wherein said anchor molecule is a transmembrane portion of a transmembrane protein.

* * * * *

SEQUENCE LISTING

```
<160> NUMBER OF SEQ ID NOS:  6

<210> SEQ ID NO 1
<211> LENGTH: 1800
<212> TYPE: DNA
<213> ORGANISM: Homo sapiens
<220> FEATURE:
<221> NAME/KEY: mRNA
<222> LOCATION: (1)..(1800)
<221> NAME/KEY: gene
<222> LOCATION: (36)..(1800)
<221> NAME/KEY: sig_peptide
<222> LOCATION: (36)..(101)
<221> NAME/KEY: CDS
<222> LOCATION: (36)..(1538)
<221> NAME/KEY: mat_peptide
<222> LOCATION: (102)..(1535)
<221> NAME/KEY: conflict
<222> LOCATION: (1034)
<221> NAME/KEY: mutation
<222> LOCATION: (1064)..(1285)
<221> NAME/KEY: conflict
<222> LOCATION: (1323)
<221> NAME/KEY: variation
<222> LOCATION: (1473)

<400> SEQUENCE: 1
ccagaagttt ggagtccgct gacgtcgccg cccag atg gcc tcc agg ctg acc          53
                                      Met Ala Ser Arg Leu Thr
                                          -20 ctg ctg acc ctc ctg ctg ctg ctg gct ggg gat aga gcc tcc tca            101
Leu Leu Thr Leu Leu Leu Leu Leu Ala Gly Asp Arg Ala Ser Ser
    -15                 -10                 -5                  -1 aat cca aat gct acc agc tcc agc tcc cag gat cca gag agt ttg caa        149
Asn Pro Asn Ala Thr Ser Ser Ser Ser Gln Asp Pro Glu Ser Leu Gln
 1               5                   10                  15 gac aga ggc gaa ggg aag gtc gca aca aca gtt atc tcc aag atg cta        197
Asp Arg Gly Glu Gly Lys Val Ala Thr Thr Val Ile Ser Lys Met Leu
                 20                  25                  30 ttc gtt gaa ccc atc ctg gag gtt tcc agc ttg ccg aca acc aac tca        245
Phe Val Glu Pro Ile Leu Glu Val Ser Ser Leu Pro Thr Thr Asn Ser
             35                  40                  45 aca acc aat tca gcc acc aaa ata aca gct aat acc act gat gaa ccc        293
Thr Thr Asn Ser Ala Thr Lys Ile Thr Ala Asn Thr Thr Asp Glu Pro
         50                  55                  60 acc aca caa ccc acc aca gag ccc acc acc caa ccc acc atc caa ccc        341
Thr Thr Gln Pro Thr Thr Glu Pro Thr Thr Gln Pro Thr Ile Gln Pro
 65                  70                  75                  80 acc caa cca act acc cag ctc cca aca gat tct cct acc cag ccc act        389
Thr Gln Pro Thr Thr Gln Leu Pro Thr Asp Ser Pro Thr Gln Pro Thr
```

-continued

```
                85                      90                      95
act ggg tcc ttc tgc cca gga cct gtt act ctc tgc tct gac ttg gag         437
Thr Gly Ser Phe Cys Pro Gly Pro Val Thr Leu Cys Ser Asp Leu Glu
            100                     105                     110 agt cat tca aca gag gcc gtg ttg ggg gat gct ttg gta gat ttc tcc         485
Ser His Ser Thr Glu Ala Val Leu Gly Asp Ala Leu Val Asp Phe Ser
            115                     120                     125 ctg aag ctc tac cac gcc ttc tca gca atg aag aag gtg gag acc aac         533
Leu Lys Leu Tyr His Ala Phe Ser Ala Met Lys Lys Val Glu Thr Asn
    130                     135                     140 atg gcc ttt tcc cca ttc agc atc gcc agc ctc ctt acc cag gtc ctg         581
Met Ala Phe Ser Pro Phe Ser Ile Ala Ser Leu Leu Thr Gln Val Leu
145                     150                     155                 160 ctc ggg gct ggg cag aac acc aaa aca aac ctg gag agc atc ctc tct         629
Leu Gly Ala Gly Gln Asn Thr Lys Thr Asn Leu Glu Ser Ile Leu Ser
            165                     170                     175 tac ccc aag gac ttc acc tgt gtc cac cag gcc ctg aag ggc ttc acg         677
Tyr Pro Lys Asp Phe Thr Cys Val His Gln Ala Leu Lys Gly Phe Thr
            180                     185                     190 acc aaa ggt gtc acc tca gtc tct cag atc ttc cac agc cca gac ctg         725
Thr Lys Gly Val Thr Ser Val Ser Gln Ile Phe His Ser Pro Asp Leu
            195                     200                     205 gcc ata agg gac acc ttt gtg aat gcc tct cgg acc ctg tac agc agc         773
Ala Ile Arg Asp Thr Phe Val Asn Ala Ser Arg Thr Leu Tyr Ser Ser
    210                     215                     220 agc ccc aga gtc cta agc aac aac agt gac gcc aac ttg gag ctc atc         821
Ser Pro Arg Val Leu Ser Asn Asn Ser Asp Ala Asn Leu Glu Leu Ile
225                     230                     235                 240 aac acc tgg gtg gcc aag aac acc aac aac aag atc agc cgg ctg cta         869
Asn Thr Trp Val Ala Lys Asn Thr Asn Asn Lys Ile Ser Arg Leu Leu
            245                     250                     255 gac agt ctg ccc tcc gat acc cgc ctt gtc ctc ctc aat gct atc tac         917
Asp Ser Leu Pro Ser Asp Thr Arg Leu Val Leu Leu Asn Ala Ile Tyr
            260                     265                     270 ctg agt gcc aag tgg aag aca aca ttt gat ccc aag aaa acc aga atg         965
Leu Ser Ala Lys Trp Lys Thr Thr Phe Asp Pro Lys Lys Thr Arg Met
            275                     280                     285 gaa ccc ttt cac ttc aaa aac tca gtt ata aaa gtg ccc atg atg aat        1013
Glu Pro Phe His Phe Lys Asn Ser Val Ile Lys Val Pro Met Met Asn
    290                     295                     300 agc aag aag tac cct gtg gcc cat ttc att gac caa act ttg aaa gcc        1061
Ser Lys Lys Tyr Pro Val Ala His Phe Ile Asp Gln Thr Leu Lys Ala
305                     310                     315                 320 aag gtg ggg cag ctg cag ctc tcc cac aat ctg agt ttg gtg atc ctg        1109
Lys Val Gly Gln Leu Gln Leu Ser His Asn Leu Ser Leu Val Ile Leu
            325                     330                     335 gta ccc cag aac ctg aaa cat cgt ctt gaa gac atg gaa cag gct ctc        1157
Val Pro Gln Asn Leu Lys His Arg Leu Glu Asp Met Glu Gln Ala Leu
            340                     345                     350 agc cct tct gtt ttc aag gcc atc atg gag aaa ctg gag atg tcc aag        1205
Ser Pro Ser Val Phe Lys Ala Ile Met Glu Lys Leu Glu Met Ser Lys
            355                     360                     365 ttc cag ccc act ctc cta aca cta ccc cgc atc aaa gtg acg acc agc        1253
Phe Gln Pro Thr Leu Leu Thr Leu Pro Arg Ile Lys Val Thr Thr Ser
    370                     375                     380 cag gat atg ctc tca atc atg gag aaa ttg gaa ttc ttc gat ttt tct        1301
Gln Asp Met Leu Ser Ile Met Glu Lys Leu Glu Phe Phe Asp Phe Ser
385                     390                     395                 400 tat gac ctt aac ctg tgt ggg ctg aca gag gac cca gat ctt cag gtt        1349
```

```
                                                                                    -continued Tyr Asp Leu Asn Leu Cys Gly Leu Thr Glu Asp Pro Asp Leu Gln Val
                405                 410                 415 tct gcg atg cag cac cag aca gtg ctg gaa ctg aca gag act ggg gtg        1397
Ser Ala Met Gln His Gln Thr Val Leu Glu Leu Thr Glu Thr Gly Val
                420                 425                 430 gag gcg gct gca gcc tcc gcc atc tct gtg gcc cgc acc ctg ctg gtc        1445
Glu Ala Ala Ala Ser Ala Ile Ser Val Ala Arg Thr Leu Leu Val
                435                 440                 445 ttt gaa gtg cag cag ccc ttc ctc ttc gtc ctc tgg gac cag cag cac        1493
Phe Glu Val Gln Gln Pro Phe Leu Phe Val Leu Trp Asp Gln Gln His
    450                 455                 460 aag ttc cct gtc ttc atg ggg cga gta tat gac ccc agg gcc tga            1538
Lys Phe Pro Val Phe Met Gly Arg Val Tyr Asp Pro Arg Ala
465                 470                 475 gacctgcagg atcaggttag ggcgagcgct acctctccag cctcagctct cagttgcagc     1598
cctgctgctg cctgcctgga cttgcccctg ccacctcctg cctcaggtgt ccgctatcca     1658
ccaaaagggc tcctgagggt ctgggcaagg gacctgcttc tattagccct ctccatggc     1718 cctgccatgc tctccaaacc actttttgca gctttctcta gttcaagttc accagactct   1778
ataaataaaa cctgacagac ca                                              1800

<210> SEQ ID NO 2
<211> LENGTH: 500
<212> TYPE: PRT
<213> ORGANISM: Homo sapiens

<400> SEQUENCE: 2

Met Ala Ser Arg Leu Thr Leu Leu Thr Leu Leu Leu Leu Leu Leu Ala
1               5                   10                  15

Gly Asp Arg Ala Ser Ser Asn Pro Asn Ala Thr Ser Ser Ser Ser Gln
                20                  25                  30

Asp Pro Glu Ser Leu Gln Asp Arg Gly Glu Gly Lys Val Ala Thr Thr
            35                  40                  45

Val Ile Ser Lys Met Leu Phe Val Glu Pro Ile Leu Glu Val Ser Ser
        50                  55                  60

Leu Pro Thr Thr Asn Ser Thr Thr Asn Ser Ala Thr Lys Ile Thr Ala
65                  70                  75                  80

Asn Thr Thr Asp Glu Pro Thr Thr Gln Pro Thr Thr Glu Pro Thr Thr
                85                  90                  95

Gln Pro Thr Ile Gln Pro Thr Gln Pro Thr Thr Gln Leu Pro Thr Asp
            100                 105                 110

Ser Pro Thr Gln Pro Thr Thr Gly Ser Phe Cys Pro Gly Pro Val Thr
        115                 120                 125

Leu Cys Ser Asp Leu Glu Ser His Ser Thr Glu Ala Val Leu Gly Asp
    130                 135                 140

Ala Leu Val Asp Phe Ser Leu Lys Leu Tyr His Ala Phe Ser Ala Met
145                 150                 155                 160

Lys Lys Val Glu Thr Asn Met Ala Phe Ser Pro Phe Ser Ile Ala Ser
                165                 170                 175

Leu Leu Thr Gln Val Leu Leu Gly Ala Gly Gln Asn Thr Lys Thr Asn
            180                 185                 190

Leu Glu Ser Ile Leu Ser Tyr Pro Lys Asp Phe Thr Cys Val His Gln
        195                 200                 205

Ala Leu Lys Gly Phe Thr Thr Lys Gly Val Thr Ser Val Ser Gln Ile
    210                 215                 220
```

-continued

```
Phe His Ser Pro Asp Leu Ala Ile Arg Asp Thr Phe Val Asn Ala Ser
225                 230                 235                 240

Arg Thr Leu Tyr Ser Ser Pro Arg Val Leu Ser Asn Asn Ser Asp
                245                 250                 255

Ala Asn Leu Glu Leu Ile Asn Thr Trp Val Ala Lys Asn Thr Asn Asn
                260                 265                 270

Lys Ile Ser Arg Leu Leu Asp Ser Leu Pro Ser Asp Thr Arg Leu Val
                275                 280                 285

Leu Leu Asn Ala Ile Tyr Leu Ser Ala Lys Trp Lys Thr Thr Phe Asp
290                 295                 300

Pro Lys Lys Thr Arg Met Glu Pro Phe His Phe Lys Asn Ser Val Ile
305                 310                 315                 320

Lys Val Pro Met Met Asn Ser Lys Lys Tyr Pro Val Ala His Phe Ile
                325                 330                 335

Asp Gln Thr Leu Lys Ala Lys Val Gly Gln Leu Gln Leu Ser His Asn
                340                 345                 350

Leu Ser Leu Val Ile Leu Val Pro Gln Asn Leu Lys His Arg Leu Glu
                355                 360                 365

Asp Met Glu Gln Ala Leu Ser Pro Ser Val Phe Lys Ala Ile Met Glu
370                 375                 380

Lys Leu Glu Met Ser Lys Phe Gln Pro Thr Leu Thr Leu Pro Arg
385                 390                 395                 400

Ile Lys Val Thr Thr Ser Gln Asp Met Leu Ser Ile Met Glu Lys Leu
                405                 410                 415

Glu Phe Phe Asp Phe Ser Tyr Asp Leu Asn Leu Cys Gly Leu Thr Glu
                420                 425                 430

Asp Pro Asp Leu Gln Val Ser Ala Met Gln His Gln Thr Val Leu Glu
                435                 440                 445

Leu Thr Glu Thr Gly Val Glu Ala Ala Ala Ser Ala Ile Ser Val
                450                 455                 460

Ala Arg Thr Leu Leu Val Phe Glu Val Gln Gln Pro Phe Leu Phe Val
465                 470                 475                 480

Leu Trp Asp Gln Gln His Lys Phe Pro Val Phe Met Gly Arg Val Tyr
                485                 490                 495

Asp Pro Arg Ala
            500

<210> SEQ ID NO 3
<211> LENGTH: 1788
<212> TYPE: DNA
<213> ORGANISM: Mus musculus
<220> FEATURE:
<221> NAME/KEY: mRNA
<222> LOCATION: (1)..(1773)
<221> NAME/KEY: CDS
<222> LOCATION: (49)..(1563)

<400> SEQUENCE: 3
ctagtgacca agaacttgga ccaggacgca gctgacatgc ctgcccag atg gcc tcc    57
                                                    Met Ala Ser
                                                      1 agg ctg acc cca ctg acc ctc ctg ctg ctg ctg gct ggg gat aga         105
Arg Leu Thr Pro Leu Thr Leu Leu Leu Leu Leu Ala Gly Asp Arg
      5                  10                  15 gcc ttc tca gat ccc gaa gct acc agc cac agc acc cag gat cca ctg    153
Ala Phe Ser Asp Pro Glu Ala Thr Ser His Ser Thr Gln Asp Pro Leu
 20                  25                  30                  35
```

-continued

| | |
|---|---|
| gag gct caa gcg aaa agc aga gag agc ttc cct gaa aga gat gac tcc<br>Glu Ala Gln Ala Lys Ser Arg Glu Ser Phe Pro Glu Arg Asp Asp Ser<br>40 45 50 | 201 |
| tgg agt ccc cca gag cct aca gta ctg ccc tct acc tgg cca aca acc<br>Trp Ser Pro Pro Glu Pro Thr Val Leu Pro Ser Thr Trp Pro Thr Thr<br>55 60 65 | 249 |
| agt gta gcc atc aca ata aca aat gac acc atg ggt aaa gta gcc aac<br>Ser Val Ala Ile Thr Ile Thr Asn Asp Thr Met Gly Lys Val Ala Asn<br>70 75 80 | 297 |
| gag tcc ttc agc cag cac agc cag cca gct gct cag cta ccc aca gat<br>Glu Ser Phe Ser Gln His Ser Gln Pro Ala Ala Gln Leu Pro Thr Asp<br>85 90 95 | 345 |
| tct cca gga cag ccc cct ctg aat tct tcc agc cag ccc tcc act gcc<br>Ser Pro Gly Gln Pro Pro Leu Asn Ser Ser Ser Gln Pro Ser Thr Ala<br>100 105 110 115 | 393 |
| tca gac ttt ccc acc cag gct act act gaa ccc ttc tgc ccg gag ccg<br>Ser Asp Phe Pro Thr Gln Ala Thr Thr Glu Pro Phe Cys Pro Glu Pro<br>120 125 130 | 441 |
| ctt gct cag tgc tct gat tca gac aga gac tcc tca gag gca aag ctc<br>Leu Ala Gln Cys Ser Asp Ser Asp Arg Asp Ser Ser Glu Ala Lys Leu<br>135 140 145 | 489 |
| tca gag gct ttg aca gat ttc tct gtg aag ctc tac cac gcc ttc tca<br>Ser Glu Ala Leu Thr Asp Phe Ser Val Lys Leu Tyr His Ala Phe Ser<br>150 155 160 | 537 |
| gct acc aag atg gct aag acc aac atg gcc ttt tcc cca ttc agc att<br>Ala Thr Lys Met Ala Lys Thr Asn Met Ala Phe Ser Pro Phe Ser Ile<br>165 170 175 | 585 |
| gcc agc ctc ctc aca cag gtt ctt ctt ggg gct gga gac agc acc aag<br>Ala Ser Leu Leu Thr Gln Val Leu Leu Gly Ala Gly Asp Ser Thr Lys<br>180 185 190 195 | 633 |
| agc aac ttg gag agc atc ctt tcc tac ccc aag gat ttt gcc tgt gtc<br>Ser Asn Leu Glu Ser Ile Leu Ser Tyr Pro Lys Asp Phe Ala Cys Val<br>200 205 210 | 681 |
| cac caa gca cta aag ggc ttt tca tcc aaa ggt gtc act tct gtg tct<br>His Gln Ala Leu Lys Gly Phe Ser Ser Lys Gly Val Thr Ser Val Ser<br>215 220 225 | 729 |
| cag att ttc cac agc cca gat ctg gcc ata agg gac acc tat gtg aat<br>Gln Ile Phe His Ser Pro Asp Leu Ala Ile Arg Asp Thr Tyr Val Asn<br>230 235 240 | 777 |
| gca tct cag agc ctg tat gga agc agc ccc aga gtc ctg ggc cca gac<br>Ala Ser Gln Ser Leu Tyr Gly Ser Ser Pro Arg Val Leu Gly Pro Asp<br>245 250 255 | 825 |
| agt gct gct aac tta gaa ctc atc aac acc tgg gtg gct gag aac acc<br>Ser Ala Ala Asn Leu Glu Leu Ile Asn Thr Trp Val Ala Glu Asn Thr<br>260 265 270 275 | 873 |
| aac cat aag atc cgc aag ctg ctg gac agc ctg cct tct gac acc tgc<br>Asn His Lys Ile Arg Lys Leu Leu Asp Ser Leu Pro Ser Asp Thr Cys<br>280 285 290 | 921 |
| ctc gtc ctt ctc aat gct gtc tac ttg agt gcc aag tgg aag ata aca<br>Leu Val Leu Leu Asn Ala Val Tyr Leu Ser Ala Lys Trp Lys Ile Thr<br>295 300 305 | 969 |
| ttt gaa cca aaa aag atg atg gcg cct ttc ttc tac aaa aac tct atg<br>Phe Glu Pro Lys Lys Met Met Ala Pro Phe Phe Tyr Lys Asn Ser Met<br>310 315 320 | 1017 |
| att aaa gtg ccc atg atg agt agc gta aag tac cct gtg gcc caa ttc<br>Ile Lys Val Pro Met Met Ser Ser Val Lys Tyr Pro Val Ala Gln Phe<br>325 330 335 | 1065 |
| gat gac cat act ttg aag gcc aag gtg gga cag ctg cag ctc tct cac<br>Asp Asp His Thr Leu Lys Ala Lys Val Gly Gln Leu Gln Leu Ser His<br>340 345 350 355 | 1113 |

```
aac ctg agc ttt gtg atc gtg gta ccc gtg ttc cca aag cac caa ctt     1161
Asn Leu Ser Phe Val Ile Val Val Pro Val Phe Pro Lys His Gln Leu
                360                 365                 370 aaa gat gta gaa aag gct ctc aac ccc act gtc ttc aag gcc atc atg     1209
Lys Asp Val Glu Lys Ala Leu Asn Pro Thr Val Phe Lys Ala Ile Met
            375                 380                 385 aag aag ctg gag ctg tcc aaa ttc ctg ccc act tac ctg acg atg cct     1257
Lys Lys Leu Glu Leu Ser Lys Phe Leu Pro Thr Tyr Leu Thr Met Pro
        390                 395                 400 cat ata aaa gta aag agc agc caa gac atg ctg tca gtc atg gag aaa     1305
His Ile Lys Val Lys Ser Ser Gln Asp Met Leu Ser Val Met Glu Lys
    405                 410                 415 ctg aaa ttc ttt gac ttc act tac gat ctc aac ctg tgc ggg ctg acc     1353
Leu Lys Phe Phe Asp Phe Thr Tyr Asp Leu Asn Leu Cys Gly Leu Thr
420                 425                 430                 435 gag gac cca gat ctt cag gtg tct gcc atg aaa cac gag aca gtg ctg     1401
Glu Asp Pro Asp Leu Gln Val Ser Ala Met Lys His Glu Thr Val Leu
                440                 445                 450 gaa ctg aca gag tca ggg gtg gaa gca gct gca gcc tct gcc atc tcc     1449
Glu Leu Thr Glu Ser Gly Val Glu Ala Ala Ala Ala Ser Ala Ile Ser
            455                 460                 465 ttt ggc cga agc tta ccc atc ttt gag gtg cag cga cct ttc ctc ttc     1497
Phe Gly Arg Ser Leu Pro Ile Phe Glu Val Gln Arg Pro Phe Leu Phe
        470                 475                 480 ctg ctc tgg gac cag caa cac agg ttc cca gtc ttc atg ggt cgt gta     1545
Leu Leu Trp Asp Gln Gln His Arg Phe Pro Val Phe Met Gly Arg Val
    485                 490                 495 tat gac ccc agg ggt tga gacaggcttg ggtaaacatt gtcacccaag            1593
Tyr Asp Pro Arg Gly
500             505 cttcagctcc tccggttatt tccttgccac tgcctgcccg agccacttca agccttagga  1653
actggcagac ggaactgttt ccatccacca acccccaggg tatcaaccac ttttttgcag  1713
cttttacggt tcaaacctat caaactctac aaataaaact tgcagacatt ttcttctccc  1773
aaaaaaaaaa aaaaa                                                    1788

<210> SEQ ID NO 4
<211> LENGTH: 504
<212> TYPE: PRT
<213> ORGANISM: Mus musculus

<400> SEQUENCE: 4

Met Ala Ser Arg Leu Thr Pro Leu Thr Leu Leu Leu Leu Leu Leu Ala
 1               5                  10                  15

Gly Asp Arg Ala Phe Ser Asp Pro Glu Ala Thr Ser His Ser Thr Gln
            20                  25                  30

Asp Pro Leu Glu Ala Gln Ala Lys Ser Arg Glu Ser Phe Pro Glu Arg
        35                  40                  45

Asp Asp Ser Trp Ser Pro Pro Glu Pro Thr Val Leu Pro Ser Thr Trp
    50                  55                  60

Pro Thr Thr Ser Val Ala Ile Thr Ile Thr Asn Asp Thr Met Gly Lys
65                  70                  75                  80

Val Ala Asn Glu Ser Phe Ser Gln His Ser Gln Pro Ala Ala Gln Leu
                85                  90                  95

Pro Thr Asp Ser Pro Gly Gln Pro Pro Leu Asn Ser Ser Ser Gln Pro
            100                 105                 110

Ser Thr Ala Ser Asp Phe Pro Thr Gln Ala Thr Thr Glu Pro Phe Cys
```

```
                    115                 120                 125
Pro Glu Pro Leu Ala Gln Cys Ser Asp Ser Asp Arg Asp Ser Ser Glu
    130                 135                 140
Ala Lys Leu Ser Glu Ala Leu Thr Asp Phe Ser Val Lys Leu Tyr His
145                 150                 155                 160
Ala Phe Ser Ala Thr Lys Met Ala Lys Thr Asn Met Ala Phe Ser Pro
                165                 170                 175
Phe Ser Ile Ala Ser Leu Leu Thr Gln Val Leu Leu Gly Ala Gly Asp
                180                 185                 190
Ser Thr Lys Ser Asn Leu Glu Ser Ile Leu Ser Tyr Pro Lys Asp Phe
                195                 200                 205
Ala Cys Val His Gln Ala Leu Lys Gly Phe Ser Lys Gly Val Thr
210                 215                 220
Ser Val Ser Gln Ile Phe His Ser Pro Asp Leu Ala Ile Arg Asp Thr
225                 230                 235                 240
Tyr Val Asn Ala Ser Gln Ser Leu Tyr Gly Ser Ser Pro Arg Val Leu
                245                 250                 255
Gly Pro Asp Ser Ala Ala Asn Leu Glu Leu Ile Asn Thr Trp Val Ala
                260                 265                 270
Glu Asn Thr Asn His Lys Ile Arg Lys Leu Leu Asp Ser Leu Pro Ser
                275                 280                 285
Asp Thr Cys Leu Val Leu Asn Ala Val Tyr Leu Ser Ala Lys Trp
290                 295                 300
Lys Ile Thr Phe Glu Pro Lys Lys Met Met Ala Pro Phe Phe Tyr Lys
305                 310                 315                 320
Asn Ser Met Ile Lys Val Pro Met Met Ser Ser Val Lys Tyr Pro Val
                325                 330                 335
Ala Gln Phe Asp Asp His Thr Leu Lys Ala Lys Val Gly Gln Leu Gln
                340                 345                 350
Leu Ser His Asn Leu Ser Phe Val Ile Val Pro Val Phe Pro Lys
                355                 360                 365
His Gln Leu Lys Asp Val Glu Lys Ala Leu Asn Pro Thr Val Phe Lys
                370                 375                 380
Ala Ile Met Lys Lys Leu Glu Leu Ser Lys Phe Leu Pro Thr Tyr Leu
385                 390                 395                 400
Thr Met Pro His Ile Lys Val Lys Ser Ser Gln Asp Met Leu Ser Val
                405                 410                 415
Met Glu Lys Leu Lys Phe Phe Asp Phe Thr Tyr Asp Leu Asn Leu Cys
                420                 425                 430
Gly Leu Thr Glu Asp Pro Asp Leu Gln Val Ser Ala Met Lys His Glu
                435                 440                 445
Thr Val Leu Glu Leu Thr Glu Ser Gly Val Glu Ala Ala Ala Ser
450                 455                 460
Ala Ile Ser Phe Gly Arg Ser Leu Pro Ile Phe Glu Val Gln Arg Pro
465                 470                 475                 480
Phe Leu Phe Leu Leu Trp Asp Gln Gln His Arg Phe Pro Val Phe Met
                485                 490                 495
Gly Arg Val Tyr Asp Pro Arg Gly
                500

<210> SEQ ID NO 5
<211> LENGTH: 353
<212> TYPE: DNA
<213> ORGANISM: Homo sapiens
```

-continued

```
<220> FEATURE:
<221> NAME/KEY: CDS
<222> LOCATION: (1)..(291)

<400> SEQUENCE: 5 gga aaa tct cta act tcc aag gtc cca cca aca gtt cag aaa cct acc       48
Gly Lys Ser Leu Thr Ser Lys Val Pro Pro Thr Val Gln Lys Pro Thr
 1               5                  10                  15 aca gta aat gtt cca act aca gaa gtc tca cca act tct cag aaa acc       96
Thr Val Asn Val Pro Thr Thr Glu Val Ser Pro Thr Ser Gln Lys Thr
                20                  25                  30 acc aca aaa acc acc aca cca aat gct caa gca aca cgg agt aca cct      144
Thr Thr Lys Thr Thr Thr Pro Asn Ala Gln Ala Thr Arg Ser Thr Pro
             35                  40                  45 gtt tcc agg aca acc aag cat ttt cat gaa aca acc cca aat aaa gga      192
Val Ser Arg Thr Thr Lys His Phe His Glu Thr Thr Pro Asn Lys Gly
         50                  55                  60 agt gga acc act tca ggt act acc cgt ctt cta tct ggg cac acg tgt      240
Ser Gly Thr Thr Ser Gly Thr Thr Arg Leu Leu Ser Gly His Thr Cys
 65                  70                  75                  80 ttc acg ttg aca ggt ttg ctt ggg acg cta gta acc atg ggc ttg ctg      288
Phe Thr Leu Thr Gly Leu Leu Gly Thr Leu Val Thr Met Gly Leu Leu
                 85                  90                  95 act tagccaaaga agagttaaga agaaaataca cacaagtata cagactgttc           341
Thr ctagtttctt ag                                                        353

<210> SEQ ID NO 6
<211> LENGTH: 97
<212> TYPE: PRT
<213> ORGANISM: Homo sapiens

<400> SEQUENCE: 6

Gly Lys Ser Leu Thr Ser Lys Val Pro Pro Thr Val Gln Lys Pro Thr
 1               5                  10                  15

Thr Val Asn Val Pro Thr Thr Glu Val Ser Pro Thr Ser Gln Lys Thr
                20                  25                  30

Thr Thr Lys Thr Thr Thr Pro Asn Ala Gln Ala Thr Arg Ser Thr Pro
             35                  40                  45

Val Ser Arg Thr Thr Lys His Phe His Glu Thr Thr Pro Asn Lys Gly
         50                  55                  60

Ser Gly Thr Thr Ser Gly Thr Thr Arg Leu Leu Ser Gly His Thr Cys
 65                  70                  75                  80

Phe Thr Leu Thr Gly Leu Leu Gly Thr Leu Val Thr Met Gly Leu Leu
                 85                  90                  95

Thr
```